(12) United States Patent
Takizawa (10) Patent No.: US 8,724,270 B2
(45) Date of Patent: May 13, 2014

(54) CIRCUIT FOR DETECTING STATIC ELECTRICITY

(75) Inventor: Akira Takizawa, Ueda (JP)

(73) Assignees: S. P. M. Company, Nagano (JP); Akira Takizawa, Nagano (JP)

( * ) Notice: Subject to any disclaimer, the term of this patent is extended or adjusted under 35 U.S.C. 154(b) by 78 days.

(21) Appl. No.: 13/393,365

(22) PCT Filed: Feb. 26, 2010

(86) PCT No.: PCT/JP2010/053106
§ 371 (c)(1),
(2), (4) Date: Feb. 29, 2012

(87) PCT Pub. No.: WO2011/027581
PCT Pub. Date: Mar. 10, 2011

(65) Prior Publication Data
US 2012/0154964 A1    Jun. 21, 2012

(30) Foreign Application Priority Data

Sep. 1, 2009  (JP) ................................. 2009-201639

(51) Int. Cl.
*H02H 9/04*  (2006.01)

(52) U.S. Cl.
USPC ............ 361/56; 361/111; 361/91.1; 361/91.5

(58) Field of Classification Search
USPC .................. 361/56, 111, 91.1, 91.5
See application file for complete search history.

(56) References Cited

U.S. PATENT DOCUMENTS 4,978,826 A * 12/1990 DeRuiter et al. ............... 219/771
5,959,820 A *  9/1999 Ker et al. ....................... 361/111
6,104,048 A *  8/2000 Wang et al. .................... 257/272
7,495,873 B2 * 2/2009 Bhattacharya et al. ......... 361/56
8,107,212 B2 * 1/2012 Nelson et al. .................. 361/220
2006/0043490 A1 * 3/2006 Brauchler et al. ............. 257/355

FOREIGN PATENT DOCUMENTS

| JP | 60-220598 A | 11/1985 |
| JP | 10-153578 A | 6/1998 |
| JP | 11-352170 A | 12/1999 |
| JP | 2002-267707 A | 9/2002 |
| JP | 2004-309193 A | 11/2004 |
| JP | 3133418 U | 7/2007 |

\* cited by examiner

*Primary Examiner* — Stephen W Jackson
*Assistant Examiner* — Zeev V Kitov
(74) *Attorney, Agent, or Firm* — Birch, Stewart, Kolasch & Birch, LLP (57) ABSTRACT

In the circuit for detecting static electricity, a switch for cancelling charges on an electrode body, which detects static electricity, is not necessarily provided. The circuit (30) for detecting static electricity comprises: a P-channel FET and an N-channel FET having respective gates thereof electrically connected to each other; a direct-current power supply for driving the P-channel FET and the N-channel FET; an electrostatically charging section (39) to be electrostatically charged, the electrostatically charging section being a portion where the gates of respective P-channel FET and the N-channel FET are electrically connected to each other; and automatically resetting means (C1, C2) which makes the electrostatically charging section (39) automatically discharge the static electricity, which has charged on the electrostatically charging section, and makes it possible to have the electrostatically charging section (39) electrostatically charged again.

3 Claims, 5 Drawing Sheets

CIRCUIT FOR DETECTING STATIC ELECTRICITY

FIELD OF TECHNOLOGY

The present invention relates to a circuit for detecting static electricity.

BACKGROUND OF TECHNOLOGY

One of conventional devices for detecting static electricity is disclosed in Patent Document 1.

In the device, a P-channel MOSFET and an N-channel MOSFET are provided in an insulated chassis, gates of the both MOSFETs are connected to each other, and electrode bodies, which are provide outside of the chassis, are electrically connected to a connection line, which electrically connects the gates to each other.

A cathode of an LED is electrically connected to a drain of the N-channel MOSFET. An anode of the LED is electrically connected to a positive electrode of a direct-current power supply, and a source of the N-channel MOSFET is electrically connected to a negative electrode of the direct-current power supply.

An anode of another LED is electrically connected to a drain of the P-channel MOSFET. A cathode of another LED is electrically connected to the negative electrode of the direct-current power supply, and a source of the P-channel MOSFET is electrically connected to the positive electrode of the direct-current power supply.

When a positively-charged object is moved and closed to the above described device, the N-channel MOSFET is turned on and the LED emits light.

On the other hand, when a negatively-charged object is moved and closed to the above described device, the P-channel MOSFET is turned on and another LED emits light.

PRIOR ART DOCUMENT

Patent Document

Patent Document 1: Japanese Laid-open Patent Publication No. P11-352170.

SUMMARY OF THE INVENTION

Problems to be Solved by the Invention

In the above described conventional device, by moving an object having an electrode body, which is electrostatically charged, close to the device, one of the LEDs emits light. Further, by moving an electrostatically charged object close to the device, the device is capable of checking if the object is positively charge or negatively charged.

However, if once electrode bodies are charged, charges on the electrode bodies must be cancelled and the FETs must be turned off before starting the next detecting operation, so a switch for cancelling charges on the electrode bodies is required.

In case of the device having the switch for cancelling charges, the switch is manually operated, so an operator must be assigned to the device for detecting static electricity.

Thus, the present invention was invented to solve the above described problem of the conventional technology, and an object of the present invention is to provide a circuit for detecting static electricity, in which the switch for cancelling charges on the electrode bodies, which detects static electricity, is not necessarily provided.

Means for Solving the Problems

To achieve the object, the present invention has following structures. Namely, circuit for detecting static electricity comprises: a P-channel FET and an N-channel FET respectively having gates electrically connected to each other; a direct-current power supply for driving the P-channel FET and the N-channel FET; an electrostatically charging section to be electrostatically charged, the electrostatically charging section being a portion where the gates of respective P-channel FET and the N-channel FET are electrically connected to each other; and automatically resetting means for making the electrostatically charging section automatically discharge the static electricity, which has charged on the electrostatically charging section, the automatically resetting means making it possible to have the electrostatically charging section electrostatically charged again.

With this structure, both of positive static electricity and negative static electricity can be detected, and the static electricity, which has charged on the electrostatically charging section, can be automatically discharged, without manual operation, so that detection of positive/negative static electricity can be performed continuously.

In the circuit, the direct-current power supply has a positive electrode and a negative electrode, a plurality of capacitors may be provided between the electrodes, a capacitance on the positive electrode side may be equal to that on the negative electrode side with respect to a midpoint between the electrodes, and the electrostatically charging section may be electrically connected to the midpoint so as to constitute the automatically resetting means.

With this structure, the capacitors, which are charged by the direct-current power supply, are electrically connected to the electrostatically charging section, and a prescribed voltage is normally applied to the electrostatically charging section. Therefore, the both FETs are turned on in the normal state where the electrostatically charging section is not electrostatically charged. When the electrostatically charging section detects positive static electricity, charges of the capacitors on the positive electrode side are cancelled and voltage at the gate of the P-channel FET becomes zero. Therefore, the P-channel FET is turned off. On the other hand, when the electrostatically charging section detects negative static electricity, charges of the capacitors on the negative electrode side are cancelled and voltage at the gate of the N-channel FET becomes zero. Therefore, the N-channel FET is turned off. After the P-channel FET and the N-channel FET are turned off, if an positively- or negatively-charged object is moved away from the circuit, the capacitors are recharged to apply the prescribed voltage to the electrostatically charging section, so that the P-channel FET and the N-channel FET are turned on again. As described above, even if the electrostatically charging section is charged, charging effects can be automatically reset and detecting static electricity can be performed without manual operation.

The circuit may further comprise: a positive static electricity informing section for informing turn-off of the P-channel FET when the electrostatically charging section detects positive static electricity and the P-channel FET is turned off; and a negative static electricity informing section for informing turn-off of the N-channel FET when the electrostatically charging section detects negative static electricity and the N-channel FET is turned off.

Another circuit of the present invention comprises: a positive static electricity detecting section for detecting positive static electricity; a negative static electricity detecting section for detecting negative static electricity; the positive static electricity detecting section including an N-channel FET and a first electrostatically charging section to be electrostatically charged, which is electrically connected to a gate of the N-channel FET; the negative static electricity detecting section including a P-channel FET and a second electrostatically charging section to be electrostatically charged, which is electrically connected to a gate of the P-channel FET; a direct-current power supply for driving the P-channel FET and the N-channel FET; first automatically resetting means for making the first electrostatically charging section automatically discharge the static electricity, which has charged on the first electrostatically charging section, and making it possible to have the first electrostatically charging section electrostatically charged again; and second automatically resetting means for making the second electrostatically charging section automatically discharge the static electricity, which has charged on the second electrostatically charging section, and making it possible to have the second electrostatically charging section electrostatically charged again.

In the circuit, the direct-current power supply has a positive electrode and a negative electrode, a plurality of capacitors may be provided between the electrodes, a capacitance on the positive electrode side may be equal to that on the negative electrode side with respect to a midpoint between the electrodes, and the first electrostatically charging section may be electrically connected to the midpoint so as to constitute the first automatically resetting means; and a plurality of capacitors may be provided between the electrodes, a capacitance on the positive electrode side may be equal to that on the negative electrode side with respect to another midpoint between the electrodes, and the second electrostatically charging section may be electrically connected to the midpoint so as to constitute the second automatically resetting means.

The circuit may further comprise: a positive static electricity informing section for informing turn-off of the N-channel FET when the first electrostatically charging section detects positive static electricity and the N-channel FET is turned off; and a negative static electricity informing section for informing turn-off of the P-channel FET when the second electrostatically charging section detects negative static electricity and the P-channel FET is turned off.

Effects of the Invention

In the circuit of the present invention, both of positive static electricity and negative static electricity can be continuously detected without manual operation.

EMBODIMENTS OF THE INVENTION (First Embodiment)
Preferred embodiments of the present invention will now be described in detail with reference to the accompanying drawings.

Figure 1:
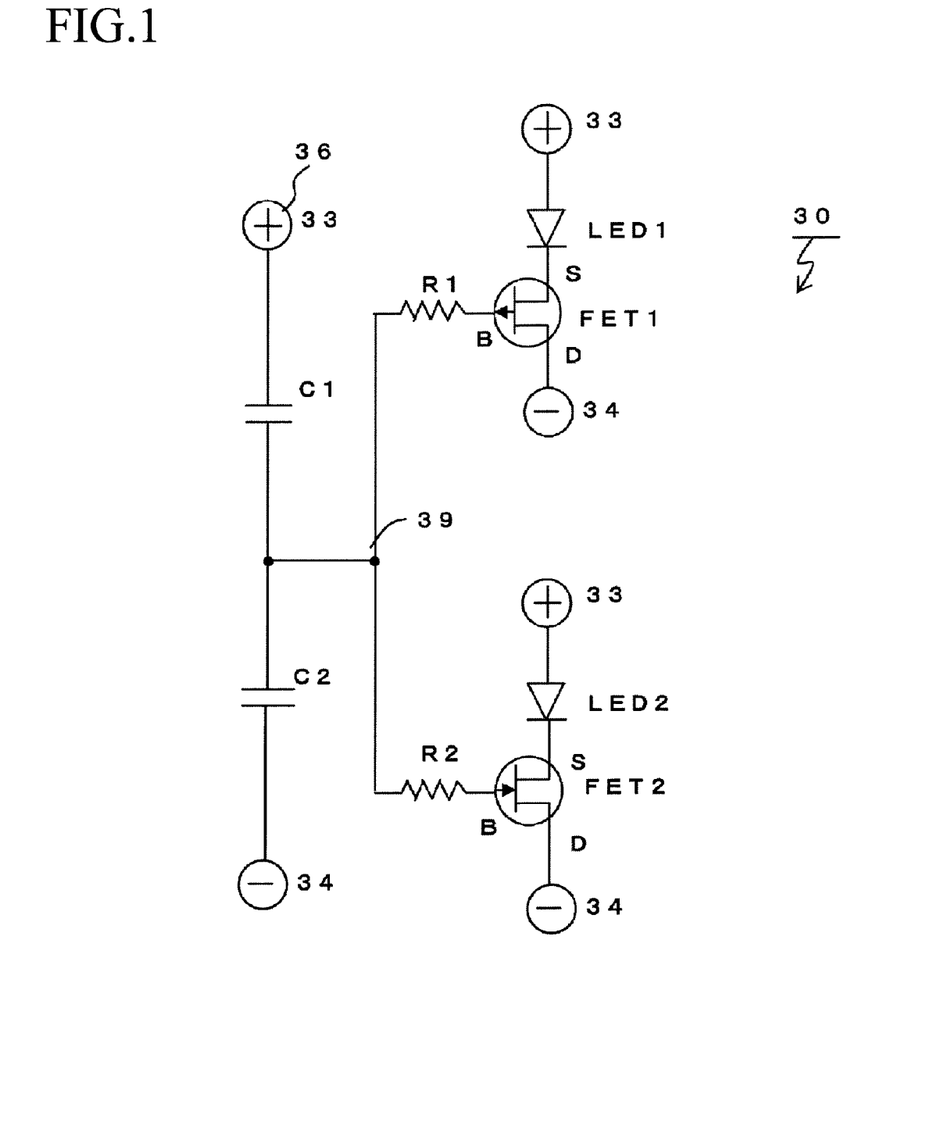
[FIG. 1] is a circuit diagram of a first embodiment of the circuit of the present invention.

FIG. 1 is a circuit diagram of the first embodiment of the circuit of the present invention.

A static electricity detecting circuit 30 includes: an FET1, which is a P-channel FET; an FET2, which is an N-channel FET; and a direct-current power supply 36 for driving the FET1 and the FET2.

A gate of the FET1 and a gate of the FET2 are connected to each other via resistances R1 and R2. A connection line, which connects the gates of the FET1 and the FET2 to each other, constitutes an electrostatically charging section 39 for detecting static electricity. The electrostatically charging section 39 may be constituted by a mere line-shaped metallic conductor (e.g., electric wire).

A plurality of capacitors C1 and C2 are serially connected between a positive electrode 33 of the direct-current power supply 36 and a negative electrode 34 thereof. The capacitors C1 and C2 have the same capacitance, and the electrostatically charging section 39 is connected to a midpoint of a connection line between the capacitors C1 and C2.

A cathode of an LED1, which informs turn-on of the FET1, is electrically connected to a source of the FET1; an anode of the LED1 is directly electrically connected to the positive electrode 33 of the direct-current power supply 36, without being connected to any resistances and capacitors.

When a prescribed drive voltage is applied to the gate of the FET1, the FET1 is turned on and an electric current flows between the source of the FET1 and a drain thereof, so that the LED1 emits light.

On the other hand, a cathode of an LED2, which informs turn-on of the FET2, is electrically connected to a drain of the FET2; an anode of the LED2 is directly electrically connected to the positive electrode 33 of the direct-current power supply 36, without being connected to any resistances and capacitors.

When a prescribed drive voltage is applied to a source of the FET2, the FET2 is turned on and an electric current flows between the drain of the FET2 and the source thereof, so that the LED2 emits light.

Note that, in the present embodiment, the FET1 and the FET2 are normally turned on, so the LED1 and the LED2 normally emit light. Colors of the LED1 and the LED2 may be different from each other so as to improve visibility.

As to the FET1, the charged voltage of the capacitor C1, which is located nearer to the negative electrode 34 of the direct-current power supply 36, is applied to the gate of the FET1, so the FET2 is normally turned on.

In case that positive static electricity exists in the vicinity of the electrostatically charging section 39, the electrostatically charging section 39 is positively electrostatically charged. Therefore, charges of the capacitor C1 are cancelled by the positive static electricity of the electrostatically charging section 39. By discharging the charges of the capacitor C1, voltage applied to the gate of the FET1 becomes zero and the FET1 is turned off. Then, the LED1 connected to the source of the FET1 is turned off, so that the positive static electricity can be detected.

Note that, prescribed drive voltage is applied to the gate of the FET2 by charges of the capacitor C2, so the FET2 is still turned on.

After discharging the capacitor C1, the capacitor C1 is recharged by the direct-current power supply 36. In this process, if positive static electricity exists in the vicinity of the electrostatically charging section 39, the capacitor C1 is not charged and the FET1 is still turned off.

In case that no positive static electricity exists in the vicinity of the electrostatically charging section 39, the capacitor C1 is charged by the direct-current power supply 36 and the FET1 is turned on. As described above, in the present embodiment, the capacitors, which are provided between the direct-current power supply and the gates of the FETs, are charged and discharged, so that the static electricity on the electrostatically charging section 39 can be automatically reset.

In case that negative static electricity exists in the vicinity of the electrostatically charging section 39, the electrostatically charging section 39 is negatively electrostatically charged. Therefore, charges of the capacitor C2 are cancelled by the negative static electricity of the electrostatically charging section 39. By discharging the charges of the capacitor C2, voltage applied to the gate of the FET2 becomes zero and the FET2 is turned off. Then, the LED2 connected to the drain of the FET2 is turned off, so that the negative static electricity can be detected.

Note that, the prescribed drive voltage is applied to the gate of the FET1 by charges of the capacitor C1, so the FET1 is still turned on.

After discharging the capacitor C2, the capacitor C2 is recharged by the direct-current power supply 36. In this process, if negative static electricity exists in the vicinity of the electrostatically charging section 39, the capacitor C2 is not charged and the FET2 is still turned off.

In case that no negative static electricity exists in the vicinity of the electrostatically charging section 39, the capacitor C1 is charged by the direct-current power supply 36 and the FET1 is turned on. As described above, in the present embodiment, the capacitors, which are provided between the direct-current power supply and the gates of the FETs, are charged and discharged, so that the static electricity on the electrostatically charging section 39 can be automatically reset.

(Second Embodiment)

Figure 2:
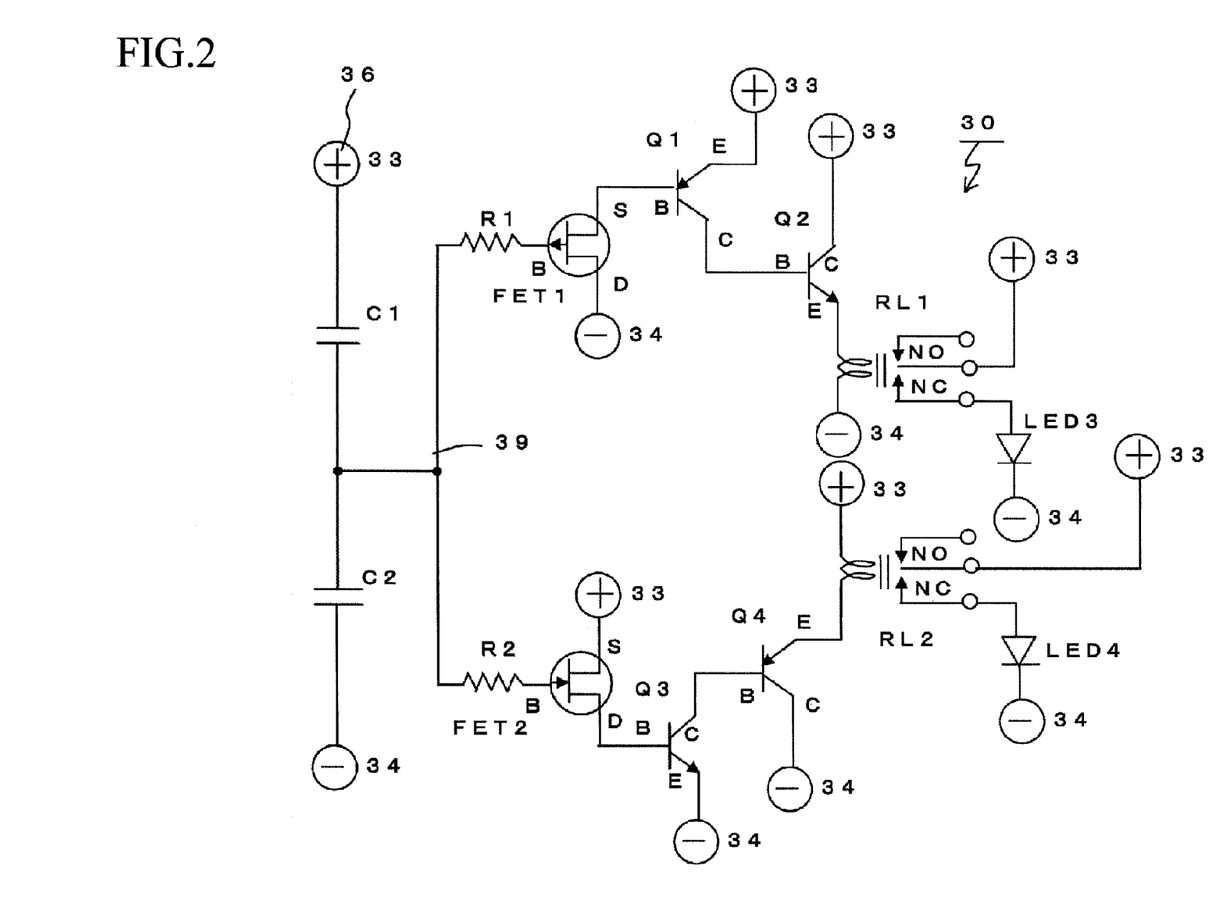
[FIG. 2] is a circuit diagram of a second embodiment of the circuit thereof.

A second embodiment of the static electricity detecting circuit 30 will be explained with reference to FIG. 2.

Note that, the structural elements described in the first embodiment are assigned the same symbols and explanation will be omitted.

In the present embodiment too, separate LEDs are used as positive static electricity informing means and negative static electricity informing means, as well as the first embodiment. Note that, in the present embodiment, the LEDs are turned off when no positive/negative static electricity is detected; one of the LEDs is emits light when positive or negative static electricity is detected.

A base of a PNP transistor Q1 is electrically connected to the source of the FET1. The positive electrode 33 of the direct-current power supply 36 is directly electrically connected to an emitter of the transistor Q1. A base of an NPN transistor Q2 is electrically connected to a collector of the transistor Q1.

The positive electrode 33 of the direct-current power supply 36 is directly electrically connected to a collector of the transistor Q2, and one end of a coil of a relay RL1 is electrically connected to an emitter of the transistor Q2. Note that, the other end of the coil of the relay RL1 is electrically connected to the negative electrode 34 of the direct-current power supply 36.

With this structure, when the FET1 is turned on, a base current of the transistor Q1 flows from the base of the transistor Q1 to the source of the FET1 and the transistor Q1 is turned on.

When the transistor Q1 is turned on, a collector current of the transistor Q1 flows to the base of the transistor Q2 and the transistor Q2 is also turned on, so that an emitter current of the transistor Q2 flows to the coil of the relay RL1.

An anode of an LED3 is electrically connected to an NC terminal of the relay RL1, and a cathode of the LED3 is electrically connected to the negative electrode 34 of the direct-current power supply 36. Further, a COM terminal or the relay RL1 is electrically connected to the positive electrode 33 of the direct-current power supply 36.

When the FET1 is turned on (when no positive static electricity is detected), the transistors Q1 and Q2 and the relay RL1 are turned on, so that the LED3, which is electrically connected to the NC terminal, is turned off.

When positive static electricity is detected on the electrostatically charging section 39, charges of the capacitor C1 are discharged and the FET1 is turned off, so that the transistors Q1 and Q2 are turned off. Then, the current passing through the relay RL1 is interrupted and the relay RL1 is closed, so that the LED3, which is electrically connected to the NC terminal, can be electrically connected to the direct-current power supply 36 and can emit light.

In case that no negative static electricity exists in the vicinity of the electrostatically charging section 39, the capacitor C2 is charged by the direct-current power supply 36 and the FET2 is turned on.

A base of an NPN transistor Q3 is electrically connected to the source of the FET2. The negative electrode 34 of the direct-current power supply 36 is directly electrically connected to an emitter of the transistor Q3. A base of a PNP transistor Q4 is electrically connected to a collector of the transistor Q3.

The negative electrode 34 of the direct-current power supply 36 is directly electrically connected to a collector of the transistor Q4, and one end of a coil of a relay RL2 is electrically connected to an emitter of the transistor Q4. Note that, the other end of the coil of the relay RL2 is electrically connected to the negative electrode 34 of the direct-current power supply 36.

With this structure, when the FET2 is turned on, a source current flows from the source of the FET2 to the base of the transistor Q3 and the transistor Q3 is turned on.

When the transistor Q3 is turned on, a base current flows from a base of the transistor Q4 to the base of the transistor Q3 and the transistor Q4 is also turned on, so that an emitter current of the transistor Q4 flows to the coil of the relay RL2.

An anode of an LED4 is electrically connected to an NC terminal of the relay RL2, and a cathode of the LED4 is electrically connected to the negative electrode 34 of the direct-current power supply 36. Further, a COM terminal of the relay RL2 is electrically connected to the positive electrode 33 of the direct-current power supply 36.

When the FET2 is turned on (when no negative static electricity is detected), the transistors Q3 and Q4 and the relay RL2 are turned on, so that the LED4, which is electrically connected to the NC terminal, is turned off.

When negative static electricity is detected on the electrostatically charging section 39, charges of the capacitor C2 are discharged and the FET2 is turned off, so that the transistors Q3 and Q4 are turned off. Then, the current passing through the relay RL2 is interrupted and the relay RL2 is closed, so that the LED4, which is electrically connected to the NC terminal, can be electrically connected to the direct-current power supply 36 and can emit light.

In case that no negative static electricity exists in the vicinity of the electrostatically charging section 39, the capacitor C2 is charged by the direct-current power supply 36 and the FET2 is turned on.

(Third Embodiment)

Figure 3:
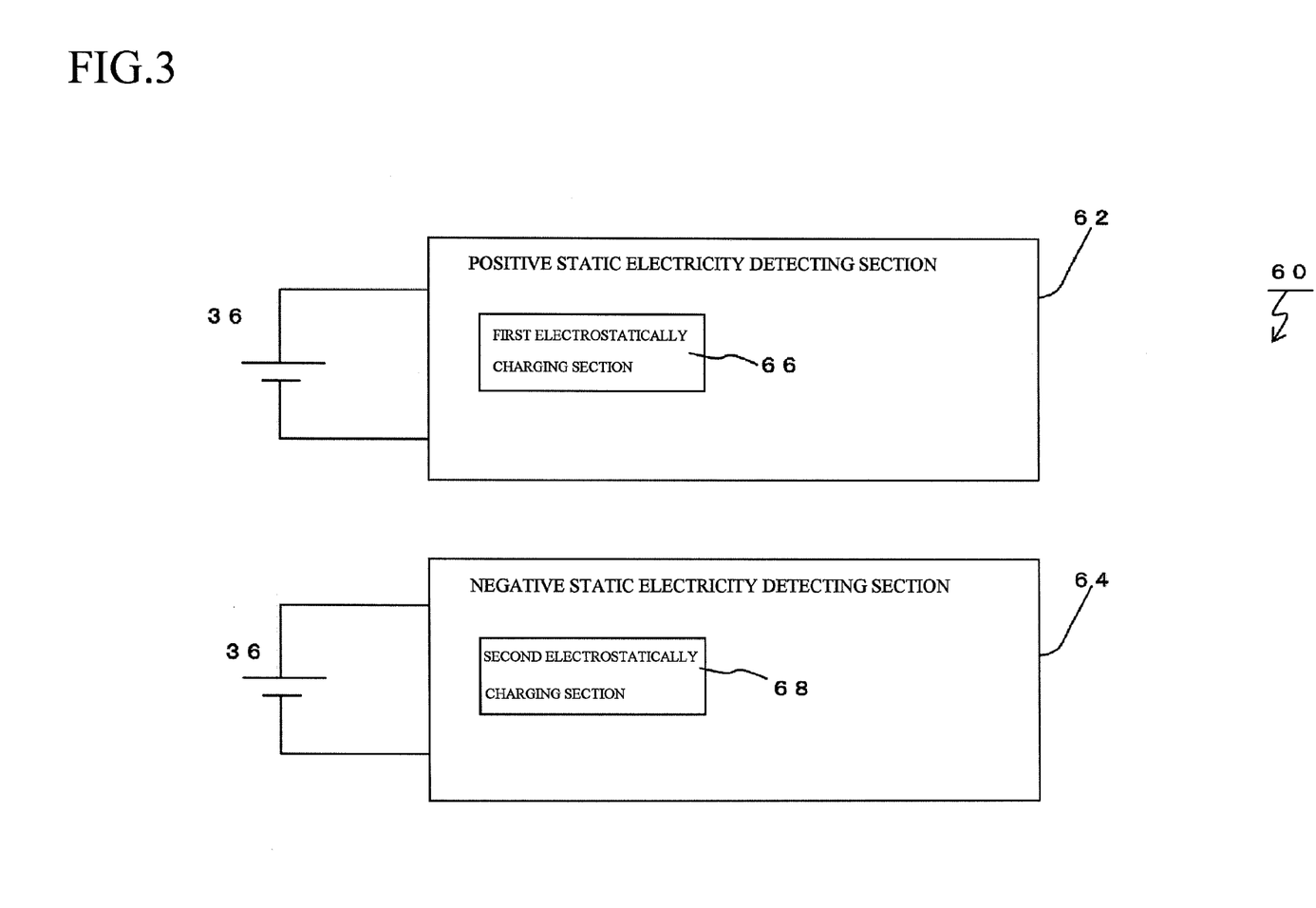
[FIG. 3] is a block diagram of a third embodiment of the circuit thereof.
Figure 4:
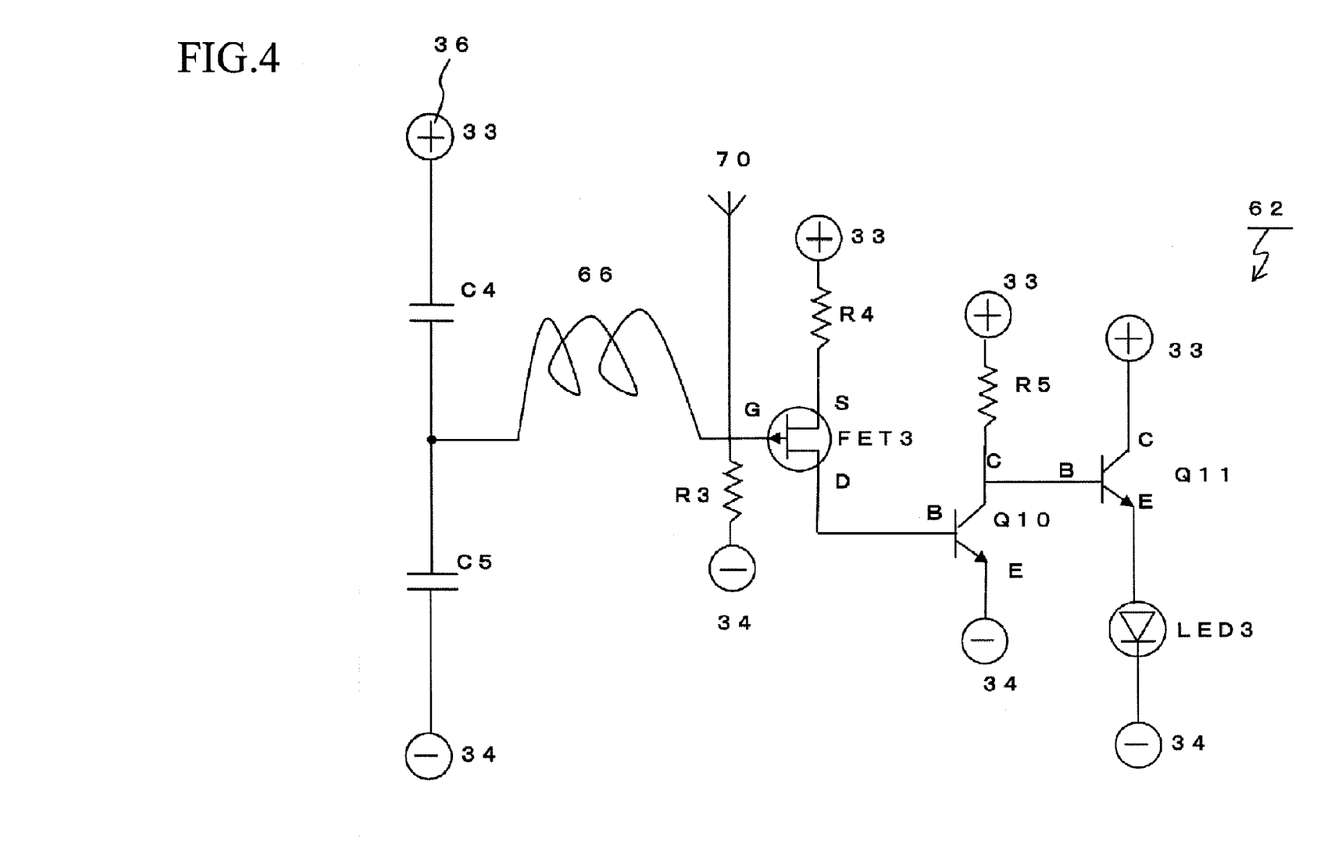
[FIG. 4] is a circuit diagram of a positive static electricity detecting section of the circuit shown in FIG. 3.
Figure 5:
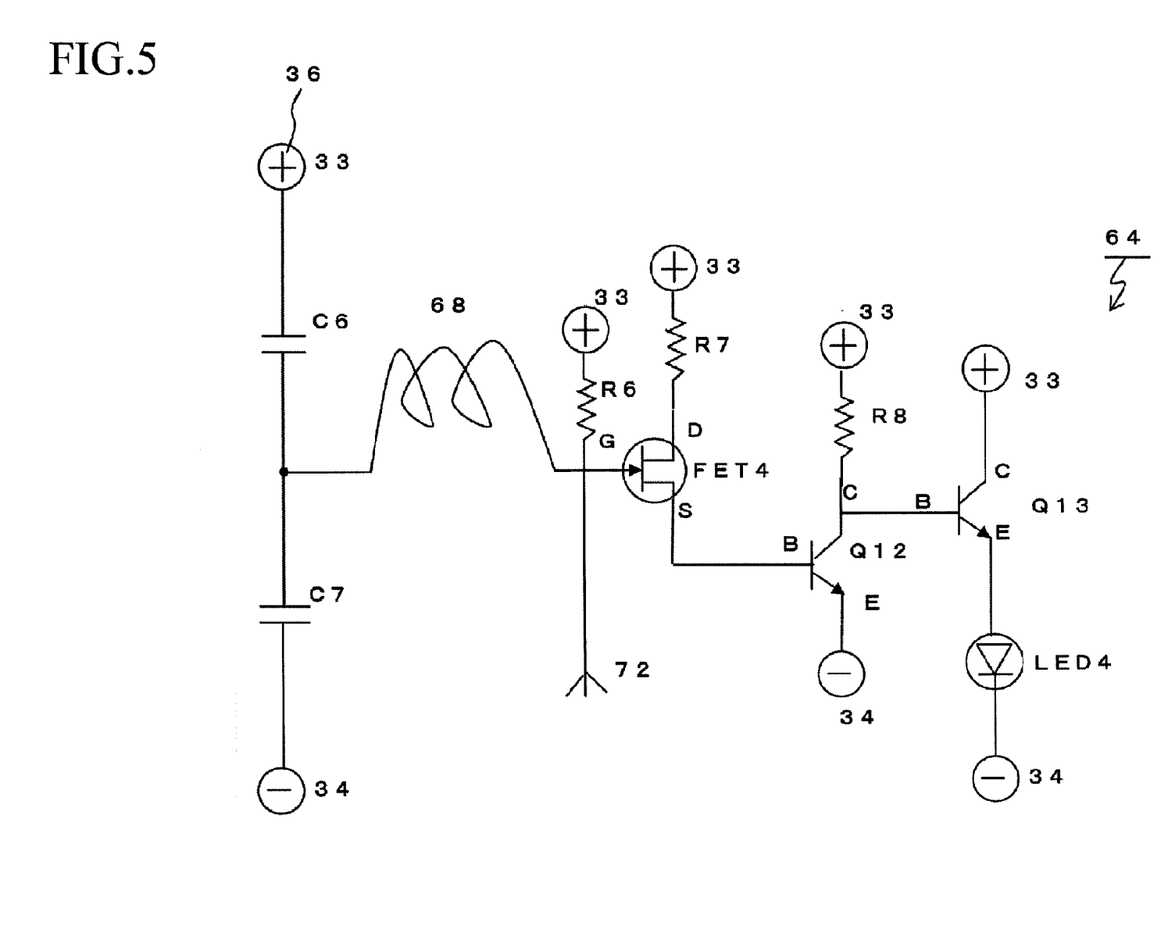
[FIG. 5] is a circuit diagram of a negative static electricity detecting section of the circuit shown in FIG. 3.

Next, a third embodiment will be explained with reference to FIGS. 3-5.

A static electricity detecting circuit 60 includes a positive static electricity detecting section 62 and a negative static electricity detecting section 64.

Firstly, the positive static electricity detecting section 62 will be explained.

The positive static electricity detecting section 62 includes an FET3, which is an N-channel FET, and a first electrostatically charging section 66, which is electrically connected to a gate of the FET3.

A plurality of capacitors C4 and C5 are serially connected between the positive electrode 33 of the direct-current power supply 36 and the negative electrode 34 thereof. The capacitors C4 and C5 have the same capacitance, and the first electrostatically charging section 66 has one end, which is electrically connected to the gate of the FET3, and the other end, which is electrically connected to a midpoint of a line connecting the capacitors C4 and C5 to each other.

The first electrostatically charging section 66 may be constituted by a mere line-shaped metallic conductor (e.g., electric wire).

The negative electrode 34 of the direct-current power supply 36 is electrically connected to a line connecting the gate of the FET3 and the first electrostatically charging section 66 to each other via a resistance R3.

The positive electrode 33 of the direct-current power supply 36 is electrically connected to the source of the FET3 via a resistance R4.

A base of an NPN transistor Q10 is electrically connected to the drain of the FET3. The positive electrode 33 of the direct-current power supply 36 is connected to a collector of the NPN transistor Q10 via a resistance R5, and a base of an NPN transistor Q11 is electrically connected to a line connecting the positive electrode 33 and the collector of the NPN transistor Q10 to each other. An emitter of the NPN transistor Q10 is electrically connected to the negative electrode 34 of the direct-current power supply 36.

A collector of the NPN transistor Q11 is electrically connected to the positive electrode 33 of the direct-current power supply 36, and the LED3, which acts as the positive static electricity informing section, is electrically connected to an emitter thereof.

The anode of the LED3 is electrically connected to the emitter of the NPN transistor Q11, and the cathode of the LED3 is electrically connected to the negative electrode 34 of the direct-current power supply 36.

Next, the action of the above described positive static electricity detecting section 62 will be explained.

Since the FET3 is electrically connected to the negative electrode 34 via the resistance R3, it is normally turned on. When the first electrostatically charging section 66 is charged by positive static electricity, positive charges are applied to the gate of the FET3 and the FET3 is turned off. Further, charges of the capacitors C4 and C5 are discharged, and an electric current flows between the positive electrode 33 and the negative electrode 34 of the direct-current power supply 36.

When the FET3 is turned off, the current from the drain of the FET3 to the base of the NPN transistor Q10 is interrupted, so that the transistor Q10 is turned off. By turning off the transistor Q10, an electric current flows to the base of the NPN transistor Q11, so that the transistor Q11 is turned on.

When the NPN transistor Q11 is turned on, an electric current flows from the emitter of the transistor Q11 to the LED3, so that the LED3 emits light.

The LED3 emitting light informs that the first electrostatically charging section 66 is electrostatically charged by positive static electricity.

Note that, after the first electrostatically charging section 66 is electrostatically charged by positive static electricity and charges of the capacitors C4 and C5 are discharged, the capacitors C4 and C5 are recharged by the direct-current power supply 36. By discharging the charges of the capacitors C4 and C5, the positive static electricity on the first electrostatically charging section 66 is cancelled, so that the FET3 connected to the resistance R3 is turned on. The other end of the first electrostatically charging section 66 is connected to the line connecting the capacitors, which are provided between the electrodes of the direct-current power supply 36, and the capacitors are charged, by static electricity, and discharged, so that the static electricity on the first electrostatically charging section 66 can be automatically reset.

Next, the negative static electricity detecting section 64 will be explained.

The positive static electricity detecting section 62 includes an FET4, which is a P-channel FET, and a second electrostatically charging section 68, which is electrically connected to a gate of the FET4.

A plurality of capacitors C6 and C7 are serially connected between the positive electrode 33 of the direct-current power supply 36 and the negative electrode 34 thereof. The capacitors C6 and C7 have the same capacitance, and the second electrostatically charging section 68 has one end, which is electrically connected to the gate of the FET4, and the other end, which is electrically connected to a midpoint of a line connecting the capacitors C6 and C7 to each other.

The first electrostatically charging section 68 may be constituted by a mere line-shaped metallic conductor (e.g., electric wire).

The positive electrode 33 of the direct-current power supply 36 is electrically connected to a line connecting the gate of the FET4 and the second electrostatically charging section 68 to each other via a resistance R6.

The positive electrode 33 of the direct-current power supply 36 is electrically connected to the drain of the FET4 via a resistance R7.

A base of an NPN transistor Q12 is electrically connected to the source of the FET4. The positive electrode 33 of the direct-current power supply 36 is electrically connected to a collector of the NPN transistor Q12 via a resistance R8, and a base of an NPN transistor Q13 is electrically connected to a line connecting the positive electrode 33 and the collector of the NPN transistor Q12 to each other. An emitter of the NPN transistor Q12 is electrically connected to the negative electrode 34 of the direct-current power supply 36.

A collector of the NPN transistor Q13 is electrically connected to the positive electrode 33 of the direct-current power supply 36, and the LED4, which acts as the negative static electricity informing section, is electrically connected to an emitter thereof.

The anode of the LED4 is electrically connected to the emitter of the NPN transistor Q13, and the cathode of the LED4 is electrically connected to the negative electrode 34 of the direct-current power supply 36.

Next, the action of the above described negative static electricity detecting section 64 will be explained.

Since the FET4 is electrically connected to the positive electrode 33 via the resistance R5, it is normally turned on. When the second electrostatically charging section 68 is charged by negative static electricity, negative charges are applied to the gate of the FET4 and the FET4 is turned off. Further, charges of the capacitors C6 and C7 are discharged, and an electric current flows between the positive electrode 33 and the negative electrode 34 of the direct-current power supply 36.

When the FET4 is turned off, the current from the source of the FET4 to the base of the NPN transistor Q12 is interrupted, so that the transistor Q12 is turned off. By turning off the transistor Q12, an electric current flows to the base of the NPN transistor Q13, so that the transistor Q13 is turned on.

When the NPN transistor Q13 is turned on, an electric current flows from the emitter of the transistor Q13 to the LED4, so that the LED4 emits light.

The LED4 emitting light informs that the second electrostatically charging section 68 is electrostatically charged by negative static electricity.

Note that, after the second electrostatically charging section 68 is electrostatically charged by negative static electricity and charges of the capacitors C6 and C7 are discharged, the capacitors C6 and C7 are recharged by the direct-current power supply 36. By discharging the charges of the capacitors C6 and C7, the positive static electricity on the second electrostatically charging section 68 is cancelled, so that the FET4 connected to the resistance R5 is turned on. The other end of the second electrostatically charging section 68 is connected to the line connecting the capacitors, which are provided between the electrodes of the direct-current power supply 36, and the capacitors are charged, by static electricity, and discharged, so that the static electricity on the second electrostatically charging section 68 can be automatically reset.

A manner of connecting the transistors Q10 and Q11 to the drain of the FET3 of the positive static electricity detecting section 62 is not limited to the above described manner as far as the LED3 is turned on by turning off the FET3.

Similarly, a manner of connecting the transistors Q12 and Q13 to the drain of the FET4 of the negative static electricity detecting section 64 is not limited to the above described manner as far as the LED4 is turned on by turning off the FET4.

Preferably, the parts C4, C5, FET3, Q10, Q11, R3, R4 and R5 of the positive static electricity detecting section 62, other than the first electrostatically charging section 66, are accommodated in an electrostatically-shielded casing. Similarly, the parts C6, C7, FET4, Q12, Q13, R6, R7 and R8 of the positive static electricity detecting section 62, other than the second electrostatically charging section 68, are accommodated in an electrostatically-shielded casing.

The first electrostatically charging section 66 and the second electrostatically charging section 68 are outwardly projected from the electrostatically-shielded casings.

The capacitors C4 and C5 and the resistance R3, which are electrically connected to the gate of the FET3, are not connected on an ordinary circuit board composed of, for example, epoxy or glass epoxy, thus it is preferred that they are connected in the air or on a highly-insulated substrate. If the circuit is formed on the ordinary circuit board composed of, for example, epoxy or glass epoxy, static electricity on the first electrostatically charging section 66 will escape via the circuit board, so the static electricity cannot be detected securely.

Similarly, the capacitors C6 and C7 and the resistance R6, which are electrically connected to the gate of the FET4, are not connected on an ordinary circuit board composed of, for example, epoxy or glass epoxy, thus it is preferred that they are connected in the air or on a highly-insulated substrate.

Note that, an electrostatically charging section 70, which is separated from the first electrostatically charging section 66, branched from the first electrostatically charging section 66 and connected to the gate of the FET3, may be provided. An end of the electrostatically charging section 70 need not be connected to the line connecting the capacitors C4 and C5 to each other.

Similarly, an electrostatically charging section 72, which is separated from the second electrostatically charging section 68, branched from the second electrostatically charging section 68 and connected to the gate of the FET4, may be provided. An end of the electrostatically charging section 72 need not be connected to the line connecting the capacitors C6 and C7 to each other.

By employing the electrostatically charging sections 70 and 72, sensitivity of detecting static electricity can be improved.

EXAMPLE 1

An actual example of the circuit of the second embodiment will be explained.

Two dry batteries, whose total voltage was 3 V, were used as the direct-current power supply, and ceramic capacitors, each of which had capacitance of 3 pF, were used as the capacitors C1 and C2.

Coated metallic resistances, each of which had a resistance value of 5 GΩ, were used as the resistances R1 and R2. The FET1 was 2SJ74, and the FET2 was 2SK170.

The transistors Q1 and Q4 were 2SA1015, and the transistors Q2 and Q3 were 2SC1815.

By employing the above described electronic parts, the static electricity detecting circuit was capable of suitably and continuously detecting positive and negative static elasticity.

EXAMPLE 2

An actual example of the circuit of the third embodiment will be explained.

Two dry batteries, whose total voltage was 3 V, were used as the direct-current power supply, and ceramic capacitors, each of which had capacitance of 3 pF, were used as the capacitors C4, C5, C6 and C7.

Coated metallic resistances, each of which had a resistance value of 5 GΩ, were used as the resistances R3 and R6. The FET3 was 2SJ74, and the FET4 was 2SK170. Coated metallic resistances, each of which had a resistance value of 6.2 kΩ, were used as the resistances R4 and R7. Coated metallic resistances, each of which had a resistance value of 10 kΩ, were used as the resistances R5 and R8.

The transistors Q10, Q11, Q12 and Q13 were 2SC1815.

By employing the above described electronic parts, the static electricity detecting circuit was capable of suitably and continuously detecting positive and negative static elasticity.

Preferred embodiments of the present invention have been described, but the present invention is not limited to the above described embodiments, so many modifications can be allowed without deviating from the spirit of the invention.

What is claimed is:
1. A circuit for detecting static electricity, comprising:
a positive static electricity detecting section for detecting positive static electricity;
a negative static electricity detecting section for detecting negative static electricity;

the positive static electricity detecting section including an N-channel FET and a first electrostatically charging section to be electrostatically charged and which is electrically connected to a gate of the N-channel FET;

the negative static electricity detecting section including a P-channel FET and a second electrostatically charging section to be electrostatically charged and which is electrically connected to a gate of the P-channel FET;

a direct-current power supply for driving the P-channel FET and the N-channel FET and having a positive electrode and a negative electrode;

a first plurality of capacitors provided between the positive electrode and the negative electrode, a capacitance on a positive electrode side of the first plurality of capacitors is equal to that on a negative electrode side of the first plurality of capacitors with respect to a first midpoint between the positive electrode of the first plurality of capacitors and the negative electrode of the first plurality of capacitors, the first plurality of capacitors configured to make the first electrostatically charging section automatically discharge static electricity which has charged on the first electrostatically charging section, and making it possible for the first electrostatically charging section electrostatically to be charged again;

a second plurality of capacitors provided between the positive electrode and the negative electrode, a capacitance on a positive electrode side of the second plurality of capacitors is equal to that on a negative electrode side of the second plurality of capacitors with respect to a second midpoint between the positive electrode of the second plurality of capacitors and the negative electrode of the second plurality of capacitors, the second plurality of capacitors configured to make the second electrostatically charging section automatically discharge static electricity which has charged on the second electrostatically charging section, and making it possible to have the second electrostatically charging section electrostatically to be charged again;

a third electrostatically charging section being separated from the first electrostatically charging section and branched from the first electrostatically chargin section from the gate of the N-channel FET, the third electrostatically charging section having ends which are not connected between the first plurality of capacitors; and a fourth electrostatically charging section being separated from the second electrostatically charging section and branched from the second electrostatically charging section from the gate of the P-channel FET, the fourth electrostatically charging section having ends which are not connected between the second plurality of capacitors.

2. The circuit according to claim 1, further comprising:

a positive static electricity informing section for informing turn-off of the N-channel FET when the first electrostatically charging section detects positive static electricity and the N-channel FET is turned off; and a negative static electricity informing section for informing turn-off of the P-channel FET when the second electrostatically charging section detects negative static electricity and the P-channel FET is turned off.

3. The circuit according to claim 2, wherein the positive static electricity informing section comprises at least one first transistor and a first light emitting diode, and wherein the negative static electricity informing section comprises at least one second transistor and a second light emitting diode.

\* \* \* \* \*